(12) United States Patent
Takano et al.

(10) Patent No.: US 8,162,904 B2
(45) Date of Patent: Apr. 24, 2012

(54) NEEDLE PROTECTOR

(75) Inventors: Ritsuo Takano, Toyama (JP); Masaki Fukuda, Nakakoma-gun (JP); Takato Murashita, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 143 days.

(21) Appl. No.: 12/293,167

(22) PCT Filed: Mar. 22, 2007

(86) PCT No.: PCT/JP2007/055890
§ 371 (c)(1),
(2), (4) Date: Sep. 16, 2008

(87) PCT Pub. No.: WO2007/122958
PCT Pub. Date: Nov. 1, 2007

(65) Prior Publication Data
US 2009/0054852 A1    Feb. 26, 2009

(30) Foreign Application Priority Data

Mar. 29, 2006    (JP) .................................. 2006-092462

(51) Int. Cl.
*A61M 5/00* (2006.01)
(52) U.S. Cl. ........ 604/263; 604/110; 604/162; 604/163; 604/164.08; 604/166.01; 604/192; 604/198; 604/199
(58) Field of Classification Search ............. 604/166.01, 604/263, 110, 162, 163, 164.08, 192, 198, 604/199
See application file for complete search history.

(56) References Cited

U.S. PATENT DOCUMENTS

| 3,768,126 A | 10/1973 | Posdal |
| 4,747,831 A | 5/1988 | Kulli |

(Continued)

FOREIGN PATENT DOCUMENTS

CA    2034556    7/1992

(Continued)

OTHER PUBLICATIONS

Machine Translation of JP 2004-154364, accessed on Jun. 15, 2009.*

(Continued)

*Primary Examiner* — Bhisma Mehta
*Assistant Examiner* — Larry R Wilson
(74) *Attorney, Agent, or Firm* — Buchanan Ingersoll & Rooney PC

(57) ABSTRACT

A protector is attached for use to a needle body having a main needle body and an enlarged-diameter section having an outer diameter greater than that of the main needle body. The protector includes a platelike protector body made of a metal material. The protector body includes a first section formed with a first hole adapted to receive the needle body when the needle body is passed therethrough, a second section formed with a second hole, and a third section adapted to connect the first section and the second section. The second hole of the second section is provided with a tubular portion that permits the main needle body to pass therethrough, but prohibits the enlarged-diameter section from passing through the tubular portion. In a state in which the protector covers the needle tip, the tubular portion comes into abutment against the enlarged-diameter section, thus prohibiting the needle body from moving toward the proximal side.

17 Claims, 6 Drawing Sheets

U.S. PATENT DOCUMENTS

| | | | |
|---|---|---|---|
| 4,755,170 A | 7/1988 | Golden | |
| 4,900,307 A | 2/1990 | Kulli | |
| 4,904,242 A | 2/1990 | Kulli | |
| 4,927,414 A | 5/1990 | Kulli | |
| 4,929,241 A | 5/1990 | Kulli | |
| 4,944,725 A | 7/1990 | McDonald | |
| 4,944,731 A | 7/1990 | Cole | |
| 4,964,854 A * | 10/1990 | Luther | 604/166.01 |
| 4,978,344 A | 12/1990 | Dombrowski et al. | |
| 4,994,041 A | 2/1991 | Dombrowski et al. | |
| 4,994,046 A | 2/1991 | Wesson et al. | |
| 5,053,017 A | 10/1991 | Chamuel | |
| 5,120,321 A | 6/1992 | Oksman et al. | |
| 5,135,504 A | 8/1992 | McLees | |
| 5,183,468 A | 2/1993 | McLees | |
| 5,215,525 A | 6/1993 | Sturman | |
| 5,215,528 A | 6/1993 | Purdy et al. | |
| 5,300,045 A | 4/1994 | Plassche, Jr. | |
| 5,322,517 A | 6/1994 | Sircom et al. | |
| 5,344,408 A | 9/1994 | Partika | |
| 5,423,766 A | 6/1995 | Di Cesare | |
| 5,458,658 A | 10/1995 | Sircom | |
| 5,549,570 A | 8/1996 | Rogalsky | |
| 5,558,651 A | 9/1996 | Crawford et al. | |
| 5,599,310 A | 2/1997 | Bogert | |
| 5,611,781 A | 3/1997 | Sircom et al. | |
| 5,662,610 A | 9/1997 | Sircom | |
| 5,755,699 A | 5/1998 | Bleecher et al. | |
| 5,879,337 A | 3/1999 | Kuracina et al. | |
| 5,882,337 A | 3/1999 | Bogert et al. | |
| 6,004,294 A | 12/1999 | Brimhall et al. | |
| 6,117,108 A | 9/2000 | Woehr et al. | |
| 6,203,527 B1 | 3/2001 | Zadini et al. | |
| 6,287,278 B1 | 9/2001 | Woehr et al. | |
| 6,443,929 B1 | 9/2002 | Kuracina et al. | |
| 6,616,630 B1 * | 9/2003 | Woehr et al. | 604/110 |
| 6,629,957 B1 | 10/2003 | Wiklund | |
| 6,652,486 B2 * | 11/2003 | Bialecki et al. | 604/110 |
| 7,125,397 B2 | 10/2006 | Woehr et al. | |
| 7,214,211 B2 | 5/2007 | Woehr et al. | |
| 7,264,613 B2 | 9/2007 | Woehr et al. | |
| 7,608,057 B2 | 10/2009 | Woehr et al. | |
| 7,611,499 B2 | 11/2009 | Woehr et al. | |
| 7,625,360 B2 | 12/2009 | Woehr et al. | |
| 2003/0195471 A1 | 10/2003 | Woehr et al. | |
| 2004/0116856 A1 | 6/2004 | Woehr et al. | |
| 2005/0004532 A1 | 1/2005 | Woehr et al. | |
| 2005/0027263 A1 | 2/2005 | Woehr et al. | |
| 2006/0116638 A1 | 6/2006 | Woehr et al. | |
| 2007/0049868 A1 | 3/2007 | Woehr et al. | |
| 2007/0083159 A1 | 4/2007 | Woehr et al. | |
| 2007/0100297 A1 | 5/2007 | Woehr et al. | |
| 2007/0129689 A1 | 6/2007 | Woehr et al. | |
| 2010/0087787 A1 | 4/2010 | Woehr et al. | |

FOREIGN PATENT DOCUMENTS

| | | |
|---|---|---|
| CA | 2 044 818 | 12/1992 |
| CA | 2 033 361 | 11/2002 |
| EP | 0 352 928 A1 | 1/1990 |
| EP | 0 352 928 B1 | 12/1992 |
| EP | 0 554 841 A1 | 8/1993 |
| EP | 0 554 841 B1 | 11/1996 |
| EP | 0 750 915 A2 | 1/1997 |
| EP | 0 750 916 A2 | 1/1997 |
| EP | 0 747 085 B2 | 4/2003 |
| JP | 2003-199822 A | 7/2003 |
| JP | 2004-154364 A | 6/2004 |
| JP | 2004154364 A * | 6/2004 |
| WO | WO 90/08564 | 8/1990 |
| WO | WO 99/08742 | 2/1999 |

OTHER PUBLICATIONS

Form PCT/ISA/210 (International Search Report) dated May 1, 2007.

Form PCT/ISA/237 (Written Opinion of the International Searching Authority) dated May 1, 2007.

* cited by examiner

NEEDLE PROTECTOR

TECHNICAL FIELD

The present invention relates to a protector capable of covering the needle tip of a needle body, which is used to puncture a blood vessel or the like during, e.g., infusion or blood collection.

BACKGROUND ART

When an infusion, blood collection, or administration of a drug solution is performed on a patient, a medical needle body such as a hollow injection needle is used. The needle body is discarded after use. However, if the used needle body is discarded as is, a disposal worker or the like may possibly experience an accident, where the needle tip is erroneously stuck into the worker's finger or the like. In particular, since blood adheres to and is left on the front surface of the needle body, or on an inside portion thereof, such erroneous sticking may possibly lead to infection.

To prevent erroneous sticks, measures are taken to cap and discard the used needle body under existing circumstances. However, also when work is performed for capping the needle body, the worker must pay close attention in order to prevent the needle tip from being stuck into his or her hand. This poses a problem in that disposal of needle bodies after use requires thousands of man-hours.

To eliminate such a problem, a protector has been proposed, which can safely cover the needle tip of a needle body after use. Specifically, the protector is mounted onto a middle portion of the needle body during use of the needle body, and after use, the protector is shifted to and covers the needle tip. (See, e.g., Patent Document 1.)

The protector described in Patent Document 1 has a platelike protector body made of a metal material. The protector main body includes a first section formed with a first hole, which is adapted to receive a needle body with a generally uniform outer diameter when the needle body is passed therethrough, a second section formed with a second hole, and a third section that connects one end of the first section to the second section. The protector is configured in the following manner. Namely, while the protector covers a needle tip, a frictional force is generated or increased between the inner circumferential surface of the first hole and the outer circumferential surface of the needle body, in order to stop the protector relative to the needle body.

However, with the protector described in Patent Document 1, the inner diameter of the first hole may be excessively greater than the outer diameter of the needle body depending on, e.g., the machining accuracy of the first hole. In such a case, the outer circumferential surface of the needle body virtually does not come into contact with the inner circumferential surface of the first hole. In other words, the frictional force virtually is not generated between the outer circumferential surface of the needle body and the inner circumferential surface of the first hole. Consequently, it is likely that the protector may become disengaged from the needle body.

To solve this problem, using a different-diameter needle as a needle body has been proposed. Such a different-diameter needle is one that includes an elongate main needle body with an enlarged-diameter section provided on the distal side of the main needle body, and having an outer diameter greater than that of the main needle body. For using the different-diameter needle, while the protector covers the needle tip, the enlarged-diameter section comes into abutment against a circumferential edge of the first hole, so that the protector is stopped with respect to the needle body.

However, even if such a different-diameter needle is used, pulling (or shifting) of the needle body may occur and excessively pull the needle, thereby allowing the enlarged-diameter section to press and deform the circumferential edge of the first hole, which increases the inner diameter of the first hole. Thus, it is possible that the enlarged-diameter section may pass through the first hole, so that the protector may become disengaged from the needle body.

With the protector described in Patent Document 1, when an operation for pulling the needle body is executed, the needle body may in some cases become slanted relative to the operating direction. Thus, when the needle becomes caught by the circumferential edge of the first hole, the needle body shifts and increases sliding resistance, thereby making it hard to execute the pulling operation.

Patent Document 1: Japanese Laid-Open Patent Publication No. 2004-154364

DISCLOSURE OF INVENTION

An object of the present invention is to provide a protector that enables a needle body to smoothly move in the course of shifting from a first posture to a second posture, so that the needle can reliably be prevented from disengaging from the needle body in the second posture.

To achieve the above object, the present invention is a protector that is mounted to a needle body including an elongate main needle body and an enlarged-diameter section provided on a distal side of the main needle body and having an outer diameter greater than that of the main needle body, and which is shiftable from a first posture capable of relatively moving along a longitudinal direction of the needle body to a second posture covering a needle tip of the needle body, the protector including:

a protector body formed by bending or curving an elastic platelike member made of a metal material and including a first section formed with a first hole adapted to receive the needle body when the needle body is passed therethrough, a second section located on a proximal side of the first section and formed with a second hole adapted to receive the needle body when the needle body is passed therethrough, a third section adapted to connect one end of the first section with the second section, and a fourth section extending from the other end of the first section toward the distal side; and a cover portion including a needle tip receiving portion provided on a side of the fourth section of the protector body so as to cover the needle tip from the distal side during the second posture, and a needle body abutment portion that functions to prevent the needle tip receiving portion from covering the needle tip by abutment against an outer circumferential surface of the needle body during the first posture;

wherein the second section is provided with a tubular portion formed like a tube to project from a circumferential edge of the second hole toward a distal direction and to permit the main needle body to pass therethrough while prohibiting the enlarged-diameter section from passing therethrough; and wherein the protector is shifted from the first posture in the distal direction relative to the needle body and the needle body abutment portion passes the needle tip, whereby the protector is deformed by an elastic force of the protector body so as to assume the second posture, and in the second posture, the tubular portion comes into abutment against the enlarged-diameter section to thereby prohibit the needle body from shifting toward the distal side.

According to the invention described above, the needle body can be shifted smoothly during the course of shifting from the first posture to the second posture, and the protector can reliably be prevented from disengagement from the needle body.

Preferably, in the protector of the present invention, the tubular portion passes through and projects from the first hole toward the distal side.

This allows the needle body to be moved more smoothly in the course of shifting from the first posture to the second posture, and can reliably prevent the protector from disengagement from the needle body.

Preferably, in the protector of the present invention, a leading end of the tubular portion is located between the first hole and the second hole.

This causes a certain amount of play, which allows the needle body to move in a longitudinal direction thereof in the second posture. Thus, operability upon movement of the needle body is enhanced.

Preferably, in the protector of the present invention, the tubular portion is made of a metal material.

Since the metal material can generally suppress sliding resistance to a low level, the needle body can move more smoothly during the course of shifting from the first posture into the second posture. In addition, since the strength of the tubular portion can be increased, the needle body can reliably be prevented from moving when the needle body is in the second posture. In other words, the protector can more reliably be prevented from becoming disengaged from the needle body.

Preferably, in the protector of the present invention, an inner circumferential surface of the tubular portion is subjected to a friction reducing treatment so as to reduce frictional resistance between the outer circumferential surface of the needle body and the inner circumferential surface of the tubular portion.

This can reliably reduce the frictional resistance between the outer circumferential surface of the needle body and the inner circumferential surface of the tubular portion during movement of the needle body. Thus, the needle body can slide more smoothly along the inner circumferential surface of the tubular portion during the course of shifting from the first posture to the second posture.

Preferably, in the protector of the present invention, the cover portion is made of a resin material.

This reduces frictional resistance between the cover portion and the outer circumferential surface of the needle body when the needle body is moved into the first posture. Thus, when the protector is in the first posture, the needle body can smoothly move along the longitudinal direction (in the axial direction) thereof by means of a relatively small operative force.

Preferably, the protector of the present invention further includes an auxiliary needle tip receiving portion provided on the distal side of the needle tip receiving portion, for receiving the needle tip when the needle tip is about to move across the needle tip receiving portion and project therefrom in the distal direction during the second posture.

This makes it possible to cover the needle tip by the auxiliary needle tip receiving portion, in place of the needle tip receiving portion, if the needle tip is not covered by the needle tip receiving portion in the second posture.

BEST MODE FOR CARRYING OUT THE INVENTION

A protector according to the present invention will hereinafter be described in detail, based on preferred embodiments thereof, as illustrated in the accompanying drawings.

<First Embodiment>

Figure 1:
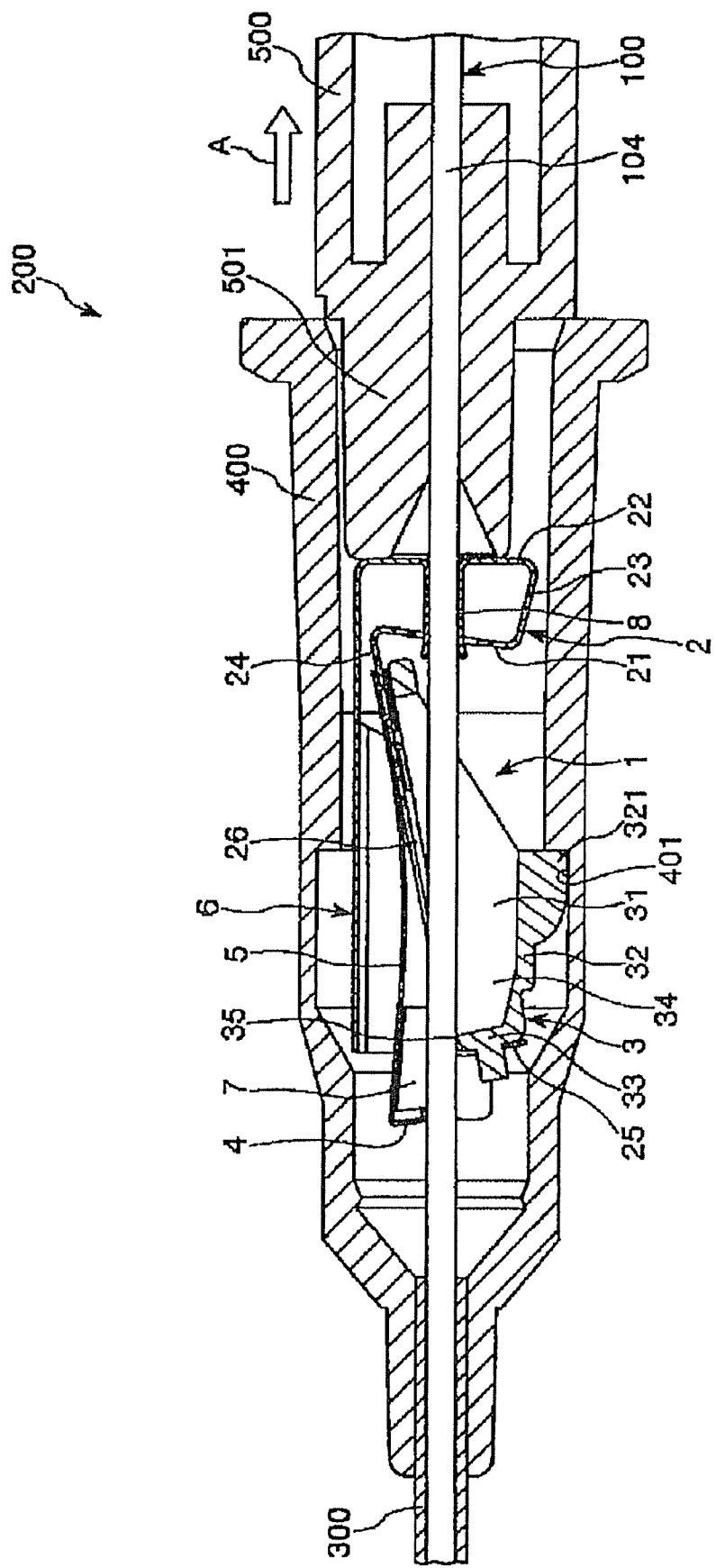
FIG. 1 is a cross-sectional lateral view illustrating a first embodiment (in a first posture) of a protector according to the present invention.
Figure 2:
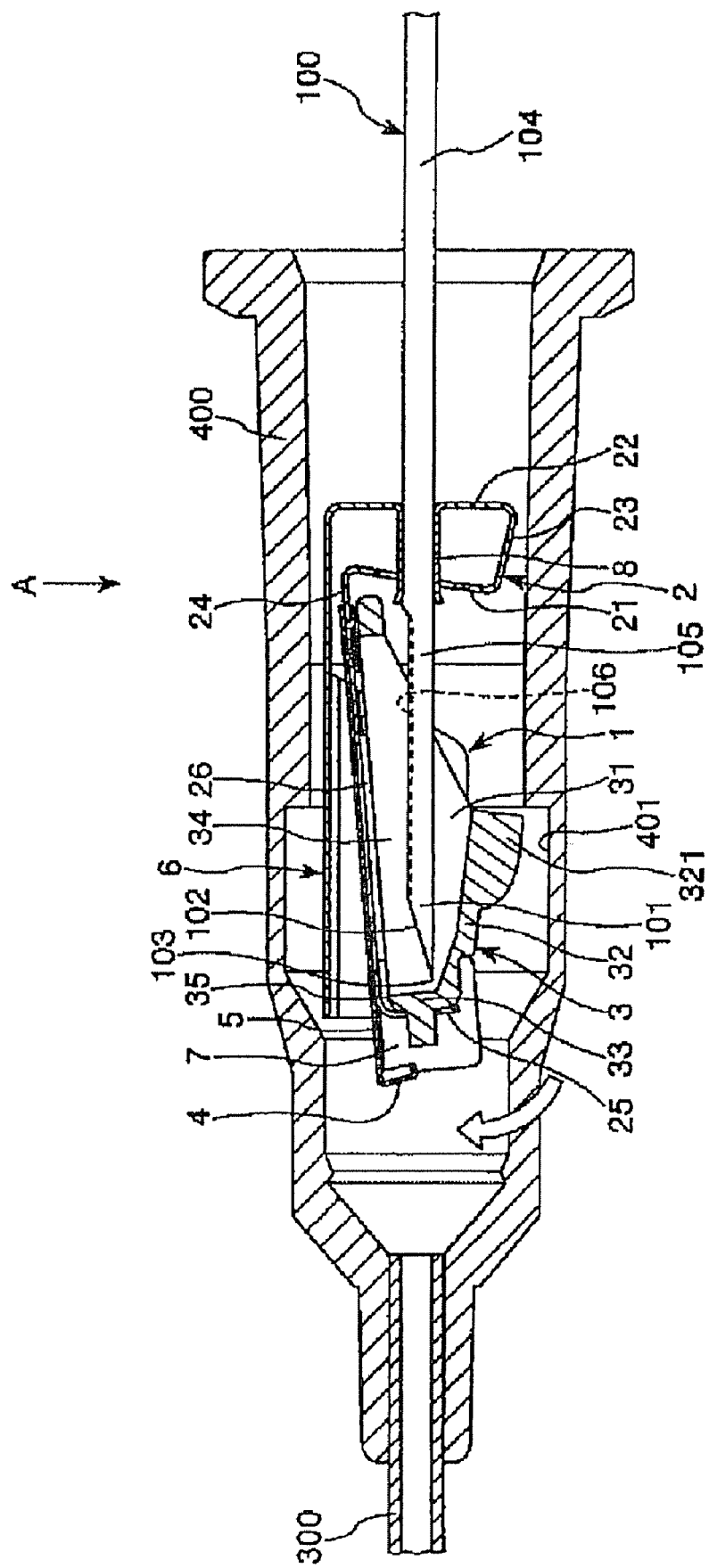
FIG. 2 is a cross-sectional lateral view illustrating the first embodiment (in a second posture) of the protector according to the invention.
Figure 3:
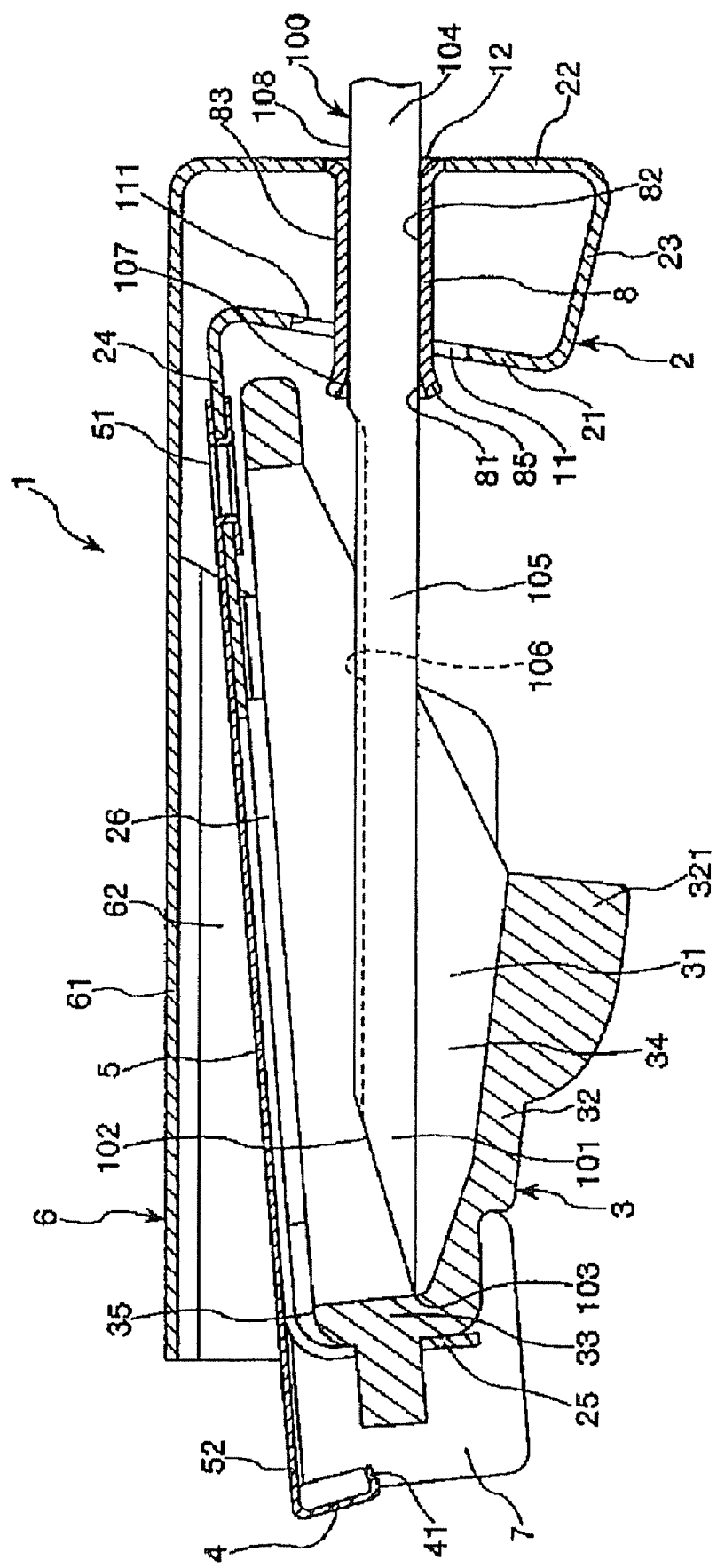
FIG. 3 is an enlarged detail view of the protector shown in FIG. 2.
Figure 4:
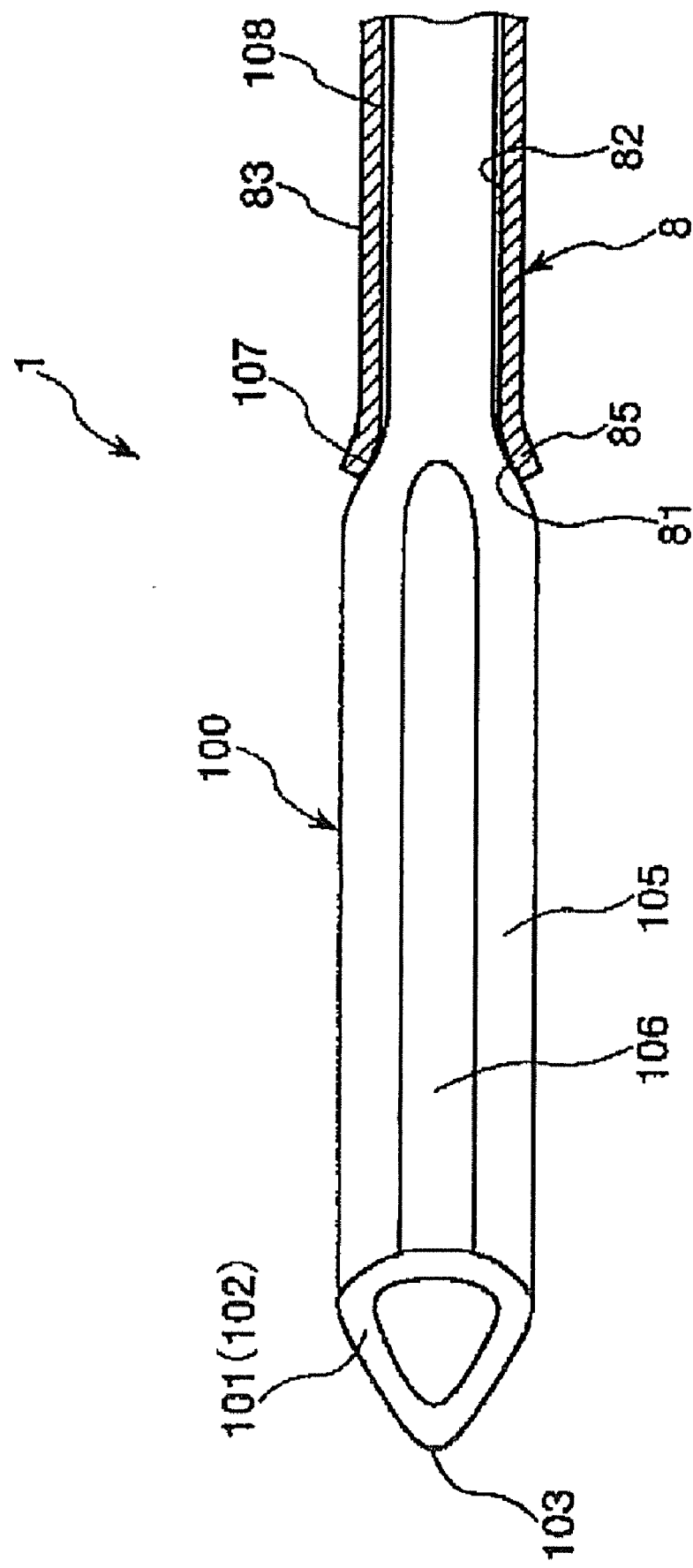
FIG. 4 is a partial, longitudinal cross-sectional view, illustrating a vicinity of a tubular portion of the protector shown in FIG. 2, as viewed from the arrow A.

FIG. 1 is a cross-sectional lateral view illustrating a first embodiment (in a first posture) of the protector according to the present invention. FIG. 2 is a cross-sectional lateral view illustrating the first embodiment (in a second posture) of the protector according to the present invention. FIG. 3 is an enlarged detail view of the protector shown in FIG. 2. FIG. 4 is a partial, longitudinal cross-sectional view, illustrating a vicinity of a tubular portion of the protector shown in FIG. 2, as viewed from the arrow A. Incidentally, descriptions are given below on the assumption that the left side, the right side, the lower side and the upper side shown in FIGS. 1 though 4 (similarly in FIG. 5) are defined as "a distal end," "a proximal end," "a first end" and "a second end," respectively.

The protector 1 illustrated in the figures is used while being attached to a needle body (a needle tube) 100 serving as an inner needle in an implant needle assembly 200, for example.

The implant needle assembly 200 shall be described prior to explaining the protector 1 of the invention.

The implant needle assembly 200 punctures and is implanted in a blood vessel or the like during, e.g., an infusion or during blood collection. This assembly 200 includes a hollow outer needle 300 or an implant needle, a tubular outer needle hub 400 disposed on a proximal side of the outer needle 300, a needle body 100 as an inner needle, which is inserted into the outer needle 300 during use thereof, and an inner needle hub 500 disposed on a proximal side of the needle body 100.

In a state (an assembled state) before the implant needle assembly 200 is used, the protector 1 is located (accommodated) in the lumen of the outer needle hub 400.

After the implant needle assembly 200 (the needle body 100) has been used, the protector 1 accommodates (covers) a needle tip 101 to prevent erroneous needle sticks or the like. As described later, the protector 1 can be displaced (deformed) to assume a first posture (the posture illustrated in FIG. 1) and a second posture (the posture illustrated in FIGS. 2 and 3). In the first posture, the protector 1 is relatively movable along the longitudinal (axial) direction of the needle body 100. In the second posture, the protector 1 covers the needle tip 101 of the needle body 100.

The needle body 100 is a hollow needle. When the needle body 100 punctures a living body (a blood vessel of a patient), for example, blood collection, infusion of a drug solution or the like can be executed. The needle body 100 includes an elongate main needle body 104, an enlarged-diameter section 105 disposed on the distal side of the main needle body 104, and a sharp needle tip 101 disposed on the distal side of the enlarged-diameter section 105.

The enlarged diameter section 105 has an outer diameter, which is greater than that of the main needle body 104, and is formed with a groove 106 therein extending along the longitudinal direction of the needle body 100. The groove 106 functions as a passage in which blood (body fluid) flows between the outer needle and the needle body, for example, when the needle body punctures and is inserted into a blood vessel. This makes it possible for flashback of the blood to be recognized, if the outer needle 300 entirely or partially enables visibility of the inside thereof, for example.

The needle tip 101 has a blade surface 102, which is slanted at a predetermined angle relative to the central axis of the needle body 100.

The needle body 100 constructed in the foregoing manner is made of a metal material, such as stainless steel, aluminum or an aluminum alloy, or titanium or a titanium alloy.

The inner needle hub 500 is secured to the proximal side of the needle body 100. The inner needle hub 500 has a columnar form in its entirety. In an assembled state, a distal end 501 of the inner needle hub 500 is located at the proximal end of the outer needle hub 400 (see FIG. 1).

The outer needle 300 is composed of a tubular body. The needle body 100 is inserted through the outer needle 300 in an assembled state.

An outer needle 300 having a certain level of flexibility preferably is used. The constituent material of the outer needle 300 preferably is a resin material, and more particularly, a soft resin material. Specific examples of the soft resin material include fluorinated resins, such as PTFE, ETFE, PFA or the like, olefin resins such as polyethylene, polypropylene or the like, or mixtures thereof, polyurethane, polyester, polyamide, polyether nylon resins, and a mixture of an olefin resin and an ethylene-vinyl acetate copolymer.

Preferably, the inside of the outer needle 300, constructed in the foregoing manner, is entirely or partially visible. More specifically, the outer needle 300 is preferably made of a transparent (uncolored transparent), colored transparent, or a semi-transparent resin. Alternatively, the outer needle 300 may have stripes, resulting from a combination of such a resin with a nontransparent resin. This makes it possible for flashback of blood, which flows inwardly from the tip opening of the outer needle 300 when the outer needle 300 enters a blood vessel, to be visibly recognized.

The outer needle hub 400 is secured to the proximal side of the outer needle 300.

Each of the constituent materials of the outer needle hub 400 and of the inner needle hub 500 is not particularly limited. Examples of such constituent materials include resin materials including polyolefins, such as polyethylene, polypropylene or ethylene-vinyl acetate copolymer, polyurethane, polyamide, polyester, polycarbonate, polybutadiene, and polyvinyl chloride.

Next, a description shall be given of the protector 1 of the present invention.

The protector 1 includes a protector body 2 and a cover portion (the first cover portion) 3, which is secured (fixed) to the protector body 2. The protector body 2 is formed by folding, or by bending, an elastic platelike member made of a metal material.

Referring to FIG. 3, the protector body 2 includes a first section 21 formed with a first hole 11, a second section 22 disposed on a proximal side (i.e., the base side of the needle) of the first section 21 and formed with a second hole 12 therein, and a third section 23 that connects one end of the first section 21 with one end of the second section 22.

The first hole 11 has a size that is sufficiently large to receive the main needle body 104 (the needle body 100), which has passed therethrough, without contact therewith. A tubular portion 8, to be described later, is installed on a circumferential edge portion of the second hole 12. Preferably, the second hole 12 is shaped circularly.

The protector body 2 further includes a fourth section 24 that extends from the other end of the first section 21 toward the distal side (generally in the distal direction). In the first and second postures, the fourth and first sections 24, 21 are arranged to form an acute angle therebetween. In this case, it is preferred that the fourth and first sections 24, 21 be biased so as to increase the acute angle formed therebetween.

In the construction shown in FIG. 3 (similarly, in FIGS. 1 and 2), the protector body 2 generally has a Z-shape formed by the fourth, first and third sections 24, 21, 23.

The protector body 2 further includes a fifth section 25, which extends downward from the distal end of the fourth section 24. In the construction shown in the figure, the fifth section 25 is provided generally vertically with respect to the fourth section 24.

The fourth section 24 is formed at a distal part with an elongate hole (notch) 26, which is adapted to receive the needle body 100 when the needle body 100 is inserted therethrough. In the first posture, the needle body 100 is inserted (passed) through the elongate hole 26 (see FIG. 1).

The above-described protector body 2 is made of a metal material. The metal material is not particularly limited. Examples of the metal material may include stainless steel, aluminum or an aluminum alloy, titanium or a titanium alloy, and copper or a copper alloy.

Incidentally, in the present embodiment, the protector body 2 is integrally formed of such sections. However, in the present invention, the protector body 2 may be composed of two or more parts that are connected to each other.

A cover portion 3 is installed on the side of the fourth section 24 of the protector body 2. Any method may be implemented for securing the fourth and fifth sections 24, to the cover portion 3. Examples of such a method include caulking, projection-recess engagement, adhesion with an adhesive, and fusion bonding.

The cover portion 3 includes a pair of first wall portions (lateral wall portions) 31, a second wall portion 32, and a third wall portion 33. The first wall portions 31 are arranged generally vertically to the fourth section 24, and located so that the needle body 100 may be placed therebetween. The second wall portion 32 is located oppositely to the fourth section 24 to enable placement of the needle body 100 therebetween. The third wall portion 33 is located at a distal end of the cover portion 3. The third wall portion 33 is disposed generally parallel to the fifth section 25 and is in contact with the inside of the fifth section 25.

A needle-tip accommodating space 34 is defined inside the cover portion 3, so as to be surrounded by the aforementioned wall portions. As shown in FIGS. 2 and 3, in the second posture, the needle tip 101 of the needle body 100 is accommodated inside of the needle-tip accommodating space 34, so that the needle body 100 may be prevented from projecting from the protector 1.

Such a cover portion 3 is displaced (shifted) integrally with the fourth and fifth sections 24, 25 when the posture of the protector 1 is changed. Such displacement causes the third and second wall portions 33, 32 of the cover portion 3 to approach toward the needle body 100 (the needle tip 101), and to shift into a position that covers the forwardmost leading end 103 of the needle tip 101 from the distal side thereof. In other words, the third and second wall portions 33, 32 enclose the needle tip 101 from the lower side shown in the figure, so as to cover the forwardmost leading end 103 of the needle tip 101 from the distal side thereof. As described above, the second and third wall portions 32, 33 of the cover portion 3 constitute a first needle tip-receiving portion (a first shutter (needle tip receiving portion)), which serves to cover the needle tip 101 from the distal side in the second posture.

The upper end of the third wall portion 33 in the figure serves as a needle body abutment portion 35, which abuts against the outer circumferential surface of the needle body 100 from the lower side of the figure, when in the first posture (see FIG. 1). A surface in contact with the needle body 100 of the needle body abutment portion 35 may be formed either as a plane or as a circular curved surface corresponding to the outer circumferential surface of the needle body 100, or to have a "V"-shape or a "U"-shape in transverse cross-section.

When in the first posture, the cover portion 3 is biased by the elasticity (springiness) of the protector body 2, so as to be turned in a clockwise direction as shown in FIG. 1. Such a biasing force brings the needle body abutment portion 35 into contact under pressure with the needle body 100 during the first posture.

In the present embodiment, the cover portion 3 (the needle body abutment portion 35 and a first needle tip receiving portion, to be described later) is made of a resin material (a synthetic resin material). Therefore, when the needle body 100 is shifted into the first posture, the frictional resistance between the needle body abutment portion 35 and the outer circumferential surface of the needle body 100 is reduced, so as to further reduce the sliding resistance of the protector 1 relative to the needle body 100. As a result, when the protector 1 assumes the first posture, the needle body 100 can move and be shifted smoothly along the longitudinal direction (the axial direction) thereof.

The resin material forming the cover portion 3 is not particularly limited. Examples of suitable resin materials include polyethylene, polypropylene, polyurethane, polystyrene, polycarbonate, polyester, an ABS resin, an AS resin, a fluorinated resin, and polyacetal.

The protector 1 is located at a middle portion (or a proximal portion) of the needle body 100 when the needle body is in the first posture, when the needle body 100 is used (to puncture a living body or the like). In the first posture, the needle body 100 is inserted (passed) from the proximal side, passing through the tubular portion 8 (the second hole 12), the first hole 11 and the elongate hole 26 in this order, whereupon the needle body 100 projects from the distal end of the protector 1.

The protector 1 is shifted from the first posture toward the distal end relative to the needle body 100, so that the protector 1 is displaced (deformed) and assumes the second posture shown in FIG. 2, covering the needle tip 101. In the second posture, an angle is formed between the fourth and first sections 24, 21 of the protector body 2, which is greater than in the first posture. In other words, the protector 1 is displaced (deformed) from the first posture and assumes the second posture by being deformed, so as to open the angle between the fourth and first sections 24, 21. Alternatively, in the second posture, an angle is formed between the first and third sections 21, 23, wherein the angle is smaller than in the first posture. In other words, the protector 1 is displaced (deformed) from the first posture and assumes the second posture by being deformed, so as to close the angle between the first and third sections 21, 23 (i.e., to bring the first section 21 closer to the third section 23). Further, alternatively, a combination thereof may be used to displace (deform) the protector 1 from the first posture into the second posture.

Additionally, the protector 1 includes a second needle tip receiving portion (a second shutter (auxiliary needle tip receiving portion)) 4, and a pair of lateral wall portions 7. The second needle tip receiving portion 4 is adapted to receive the needle tip 101 (the forwardmost leading end 103) during the second posture, assuming that the needle tip 101 is not covered by the third wall portion 33 (the first needle tip receiving portion). The lateral wall portions 7 are adapted to laterally cover the needle tip 101 (to cover the needle tip 101 while gripping it from both sides) on the proximal side (or in the vicinity of the proximal side) of the second needle tip receiving portion 4. The second needle tip receiving portion 4 is disposed on the distal sides of the third wall portion 33 and second wall portion 32 (the first needle tip receiving portion).

The second needle tip receiving portion 4 and the lateral wall portions 7 are secured to the protector body 2 via an elastic piece 5. The elastic piece 5 is a platelike member having a proximal end 51 which is joined (secured) to the fourth section 24 (see FIG. 3).

The second needle tip receiving portion 4 bends from a leading end 52 of the elastic piece 5 so as to project generally downward as shown in the figures. In other words, the second needle receiving portion 4 is bent in an L-shape (like a hook) relative to the leading end 52 of the elastic piece 5. In the present embodiment, the angle at which the second needle tip receiving portion 4 is bent is about 90°. However, the bending angle is not particularly limited. It is preferred that the bending angle normally be about 60° to 90°.

In addition, the lateral wall portions 7 are provided so as to bend from both lateral portions of the elastic piece 5, at an angle of about 90°, so that the lateral wall portions 7 project generally downward as shown in the figures.

In the present embodiment, the second needle tip receiving portion 4, the elastic piece 5 and the lateral wall portions 7 are integrally formed by bending a platelike member made of a metal material. The metal material can be the same as that used for the constituent material of the protector body 2. In addition, the constituent material used for the second needle tip receiving portion 4, the elastic piece 5 and the lateral wall portion 7 is not limited to being a metal material, but can also be composed of various synthetic resin materials. In addition, the elastic piece 5, the second needle tip receiving portion 4 and the lateral wall portions 7 may be formed of different types of materials, respectively.

The thickness of the elastic piece 5 varies in the preferable value thereof depending on conditions such as the constituent material, the outer diameter of the needle body 100, etc. Preferably, the thickness of the elastic piece 5 is smaller than the thickness of the platelike member forming the protector body 2. Specifically, it is preferred that the thickness of the elastic piece 5 normally be about 0.02 to 0.1 mm, and more preferably, about 0.04 to 0.08 mm.

In the present embodiment, the second needle tip receiving portion 4 includes a retaining portion 41 that curves (or bends) inwardly from the lower end thereof as shown in FIG. 3. When receiving the forwardmost leading end 103 of the needle tip 101, the second needle tip receiving portion 4 can more reliably prevent the forwardmost leading end 103 from escaping downwardly as shown in the figures. Since the curve surface of the retaining portion 41 comes into abutment against the outer circumferential surface of the needle body 100 during the first posture, the second needle tip receiving portion 4 (the retaining portion 41) slides smoothly relative to the needle body 100, with only a small amount of frictional resistance.

As shown in FIG. 1, during the first posture, the second needle tip receiving portion 4 is brought into contact under pressure with the outer circumferential surface of the needle body 100, from the upper side of the figure, by the elastic force of the elastic piece 5. In addition, the elastic piece 5 is elastically deformed and bent such that the distal side portion thereof is spaced apart from the fourth section 24. In addition, during the first posture, the second needle tip receiving portion 4 comes into abutment against the needle body 100 from a side opposite to the needle body abutment portion 35.

In the present embodiment, the lateral wall portions 7 are sized so as to laterally cover the needle body 100 also during the first posture. That is to say, the needle body 100 is gripped between the pair of lateral wall portions 7. This makes it possible to reliably prevent the protector 1 and the needle body 100 from becoming laterally offset from each other, during the period from the first posture to the second posture, so that the protector can smoothly and reliably assume the second posture.

As shown in FIGS. 2 and 3, when the protector assumes the second posture, the second needle tip portion 4 and the needle body 100 do not come into contact with each other. Therefore, the second needle tip receiving portion 4 is shifted by the elastic force of the elastic piece 5, in a direction of approaching toward the needle tip 101, closing the second needle tip receiving portion 4 from above as shown in the figures. In the second posture, the elastic piece 5 straightly extends so as to be located and overlap (generally parallel to) the fourth section 24.

The second needle tip receiving portion 4 is located on the distal side of the first needle tip receiving portion (the second wall portion 32 and the third wall portion 33). Therefore, the second needle tip receiving portion 4 closes before the first needle tip receiving portion closes.

When the protector is shifted from the first posture and assumes the second posture, the second wall portion 32 and third wall portion 33 of the cover portion 3 are closed from the lower side of the figures, as described above. In contrast, the second needle tip receiving portion 4 closes from the upper side of the figures. In this way, the first needle tip receiving portion and the second needle tip receiving portion 4 are closed (alternately) from sides opposite to each other. Thus, the needle tip receiving portions can receive the needle tip 101 (the forwardmost leading end 103) more reliably, so that the needle tip 101 can reliably be prevented from projecting from the protector 1 during the second posture.

The protector 1 of the present embodiment includes a cover portion (a second cover portion) 6, which at least partially covers the protector body 2 and the cover portion 3. The cover portion 6 includes a first cover section 61 and a pair of second cover sections 62 (see FIG. 3). The first cover section 61 extends from the other end (the upper end in the figures) of the second section 22, in a generally distal direction, and is disposed to cover the outside of the fourth section 24. The pair of second cover sections 62 is provided to extend downwardly in the figures, from both respective lateral sides of the first cover section 61, to cover the sides of the protector body 2 and the cover portion 3.

The cover portion 6 has a function to prevent the cover portion 3 from being removed as a result of being pinched by the fingers, as well as to prevent the elastic pieces 5 from being deformed as a result of being pinched by the fingers. Incidentally, in the present invention, the cover portion 6 may also be omitted.

The tubular portion 8 is joined to (installed on) the second section 22. The tubular portion 8 is formed in a tubular shape so as to project in the distal direction from the circumferential edge portion of the second hole 12. In both the first and second postures, the tubular portion 8 is installed with the axis thereof generally parallel to the operating direction in which the needle body 100 is pulled in the proximal direction. Incidentally, the method of joining the tubular portion 8 to the second section 22 is not particularly limited. Examples of such methods include caulking, adhesion with an adhesive, and fusion bonding.

The tubular portion 8 has an annular form in transverse cross-section. The tubular portion 8 has a cylindrical inner surface portion 82 which defines a minimum inner diameter, which is set to a value greater than the outer diameter of the main needle body, and smaller than the outer diameter of the enlarged-diameter section 105. Therefore, as shown in FIGS. 3 and 4, the main needle body 104 can pass through the tubular portion 8, but the enlarged-diameter section 105 cannot pass through the tubular portion 8. In this way, in the second posture, the tubular portion 8 reliably comes into abutment against the enlarged-diameter section 105.

Consequently, the needle body 100 is prohibited from moving toward the proximal side, and the protector 1 is reliably prevented from being removed from the needle body 100. This makes it possible for the protector 1 to cover the needle tip 101 of the needle body 100 after use, thereby eliminating accidents in which the needle tip 101 erroneously sticks a hand, a finger or the like during disposal. In short, the protector promotes excellent hygiene and safety.

In the state shown in FIGS. 3 and 4, even if it is attempted to operate (pull) the needle body 100 in the proximal direction, such an operation is impossible, because the tubular portion 8 does not become deformed such that its inner diameter increases to allow the enlarged-diameter section 105 to pass therethrough.

Preferably, the tubular portion 8 has at its distal portion 85 a tapered portion 81 having an inner diameter that gradually increases toward the distal direction thereof.

As shown in FIG. 3, the tubular portion 8 has a length greater (longer) than the interval between the first section 21 and the second section 22. In other words, the tubular portion 8 passes through the first hole 11 and projects therefrom toward the distal side. However, the tubular portion 8 may be shorter.

Incidentally, a slight gap preferably is provided between an inner circumferential surface 82 of the tubular portion 8 and an outer circumferential surface 108 of the needle body 100, so as to reduce the frictional resistance therebetween. This makes it possible to reliably reduce frictional resistance between the inner circumferential surface 82 of the tubular portion 8 and the outer circumferential surface of the needle body 100. Thus, the needle body 100 can slide more smoothly along the inner circumferential surface 82 of the tubular portion 8, in the course of being displaced from the first posture to the second posture. Alternatively, a friction reduction treatment may additionally be performed. Examples of such a treatment include application (coating) of a lubricant, such as silicone oil or the like, on the internal circumferential surface 82 of the tubular portion 8.

In the second posture (as well as in the first posture), the outer circumferential surface 83 of the tubular portion 8 is separate from the inner circumferential surface 111 of the first hole 11. This prevents the inner circumferential surface 111 of the first hole 11 from pressing the tubular portion 8 as a result of elastic deformation of the protector 1, during displacement of the protector from the first posture into the second posture. The posture of the tubular portion 8 can reliably be maintained when the axis of the tubular portion 8 is kept generally parallel to the axis of the needle body 100. Thus, the needle body 100 can smoothly be moved inside of the tubular portion 8.

The tubular portion 8 may be made of a material that is the same as that of the protector body 2, or from a material that is different from the material of the protector body 2.

If the same constituent materials (metal materials) are used, the number of different kinds of constituent materials used can be reduced in order to reduce production costs.

If different constituent materials are used, respective materials suitable for molding the tubular portion 8 and the protector body 2, for example, can be used. In this case, a material, which is superior in mechanical strength and sliding performance, should be used for the tubular portion 8.

Figure 5:
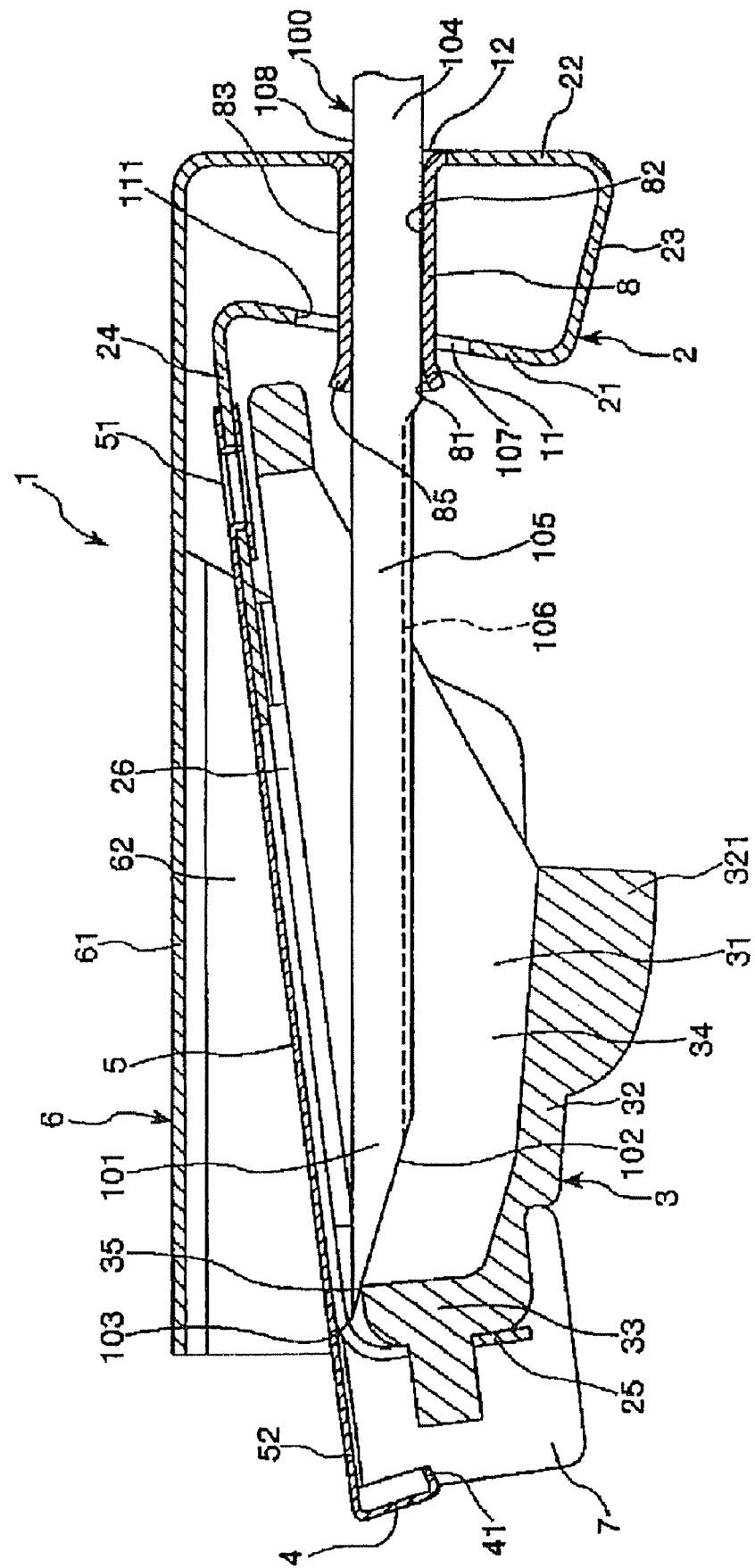
FIG. 5 is a cross-sectional lateral view (an enlarged detail view) illustrating the first embodiment (in the first posture) of the protector according to the invention.

FIG. 5 is a cross-sectional lateral view (an enlarged detail view) illustrating the first embodiment (in the first posture) of the protector according to the present invention. In the state shown in FIGS. 1 through 3, the protector 1 is mounted on the needle body 100 with the blade surface 102 of the needle tip 101 not opposed to the needle body abutment portion 35. In contrast, in order to illustrate a different point, in the state shown in FIG. 5, the protector 1 is mounted on the needle body 100 with the blade surface 102 of the needle tip 101 opposed to the needle body abutment portion 35.

In the case shown in FIGS. 1 and 2, the needle body abutment portion 35 will not come into contact with the blade surface 102. If the protector 1 is shifted from the first posture in the distal direction relative to the needle body 100, therefore, the first needle tip receiving portion (the third wall portion 33 and the second wall portion 32) closes in a single stroke (at once) when the needle body abutment portion 35 passes the forwardmost leading end 103 of the needle tip 101. In other words, the needle tip 101 is covered by the cover portion 3. In addition, at this time, since the proximal end 107 of the enlarged-diameter section 105 is fitted onto the distal portion 85 (the taper portion 81) of the tubular portion 8, further movement of the needle body 100 is stopped. In short, movement of the needle body 100 is reliably carried out until the needle body abutment portion 35 passes the forwardmost leading end 103 of the needle tip 101. Thus, the state shown in FIG. 2 can be provided in a reliable manner.

On the other hand, the blade surface 102 may face toward the lower side as shown in FIG. 5. In such a case, when the protector 1 is shifted from the first posture in the distal direction relative to the needle body 100, the first needle tip receiving portion (the first wall portion 33 and the second wall portion 32) gradually closes, while the needle body abutment portion 35 slides along the slanted blade surface 102. As a result, depending on conditions such as the shifting rate of the protector 1, the machining accuracy of the protector 1, etc., the proximal end 107 of the enlarged-diameter section 105 rarely comes into abutment against the distal end 85 (i.e., the taper portion 81) of the tubular portion 8, to thereby stop movement of the needle body 100 before the needle body abutment portion 35 passes the forwardmost leading end 103 of the needle tip 101. Assuming that such a phenomenon occurs, the forwardmost leading end 103 of the needle tip 101 will not be covered by the first needle tip receiving portion (the third wall portion 33 and the second wall portion 32), as shown in FIG. 5. In this state, if the needle body 100 is pressed in the distal direction by a strong force (a force stronger than the braking force), the needle tip 101 may be likely to project in the distal direction from the first needle tip receiving portion (the third wall portion 33 and the second wall portion 32).

However, the protector 1 is provided with the second needle tip receiving portion 4, which closes before the first needle tip receiving portion (the third wall portion 33 and the second wall portion 32) becomes closed. Therefore, even if the needle tip 101 moves across the first needle tip receiving portion (the third wall portion 33 and the second wall portion 32), the forwardmost leading end 103 comes into abutment against the inside of the second needle tip receiving portion 4, to reliably prevent the needle tip 101 from moving across the protector 1 and projecting from the protector 1 in the distal direction. Further, the lateral wall portions 7 laterally cover the needle tip 101 on the proximal side of the second needle tip receiving portion 4. Even if the needle tip 101 is about to move off to one side (laterally) relative to the protector 1, therefore, such movement can be prevented to thereby reliably prevent the needle tip 101 (the forwardmost leading end 103) from moving across the second needle tip receiving portion 4.

As described above, the protector 1 is provided with the second needle tip receiving portion 4 as well as the lateral wall portions 7. Therefore, the needle tip 101 can be prevented reliably from moving across the protector 1 and projecting therefrom in the distal direction after the protector 1 has covered the needle tip 101, regardless of conditions such as the orientation of the blade surface 102 of the needle tip 101 relative to the protector 1, or the rate and angle at which the protector 1 is shifted, etc.

Hereinafter, by way of example, a description shall be given concerning use of the aforementioned protector 1 and implant needle assembly 200.

[1] In an assembled state (i.e., the state shown in FIG. 1), the needle tip 101 of the needle body 100, and next, the needle tip (not shown) of the outer needle 300 in the implant needle assembly 200, puncture a blood vessel (vein or artery) of a patient. Thus, both of the needle tips secure the blood vessel. Securing of the blood vessel can be perceived visually by recognizing flashback of the blood, as described earlier.

[2] While the outer needle 300 that is implanted into the blood vessel is pressed with a hand, the inner needle hub 500 is gripped with the other hand, and the needle body 100 is pulled in the proximal direction. In this case, a projecting portion 321 formed on the external surface side of the second wall portion 32 of the cover portion 3 is inserted into and engaged with a recessed portion 401, which is formed on the inner circumferential surface of the outer needle hub 400. Therefore, the protector 1 connects to the outer needle hub 400, such that the protector 1 remains within the lumen of the outer needle hub 400. In this way, the protector 1 is moved in the distal direction, relative to the needle body 100.

[3] If the needle body abutment portion 35 passes the needle tip 101, the protector 1 is elastically deformed (owing to the elasticity thereof) so as to assume the second posture, as shown in FIGS. 2 and 3. When the protector 1 assumes the second posture, the tubular portion 8 comes into abutment against the enlarged-diameter section 105 as described earlier, in order to prohibit (prevent) the protector 1 from shifting in the distal direction of the needle body 100, whereby the protector 1 stops (rests) relative to the needle body 100 (see FIG. 4). Thus, the posture change of the cover portion 3 causes the projecting portion 321 to move out from the recessed portion 401, to thereby release the connected state of the protector 1 with the outer needle hub 400.

[4] If the needle body 100 is further pulled in the distal direction from the state shown in FIGS. 2 and 3, the protector 1 moves out of the outer needle hub 400 along with the needle body 100, while covering the needle tip 101 of the needle body 100, that is, while not becoming disengaged from the needle body 100.

[5] A connector or the like of an infusion set (not shown) is quickly connected to the outer needle hub 400 with the needle body 100 removed therefrom, and administration of a drug solution is started in accordance with existing regulations. After the needle body 100 has been removed from the outer needle 300, as described above, the needle body 100 is placed on a shelf, because it is unwanted. In this case, the forwardmost leading end 103 of the needle tip 101 is covered by the first needle tip receiving portion (the third wall portion 33, the second wall portion 32), or by the second needle tip receiving portion 4 from the distal side. Thus, the needle tip 101 will not move across and project from the protector 1. The function of the tubular portion 8 prevents the protector 1 from becoming disengaged from the needle tip 101. This prevents accidents from occurring, such as the needle tip 101 erroneously sticking the hand, a finger or the like, during disposal thereof.

<Second Embodiment>

Figure 6:
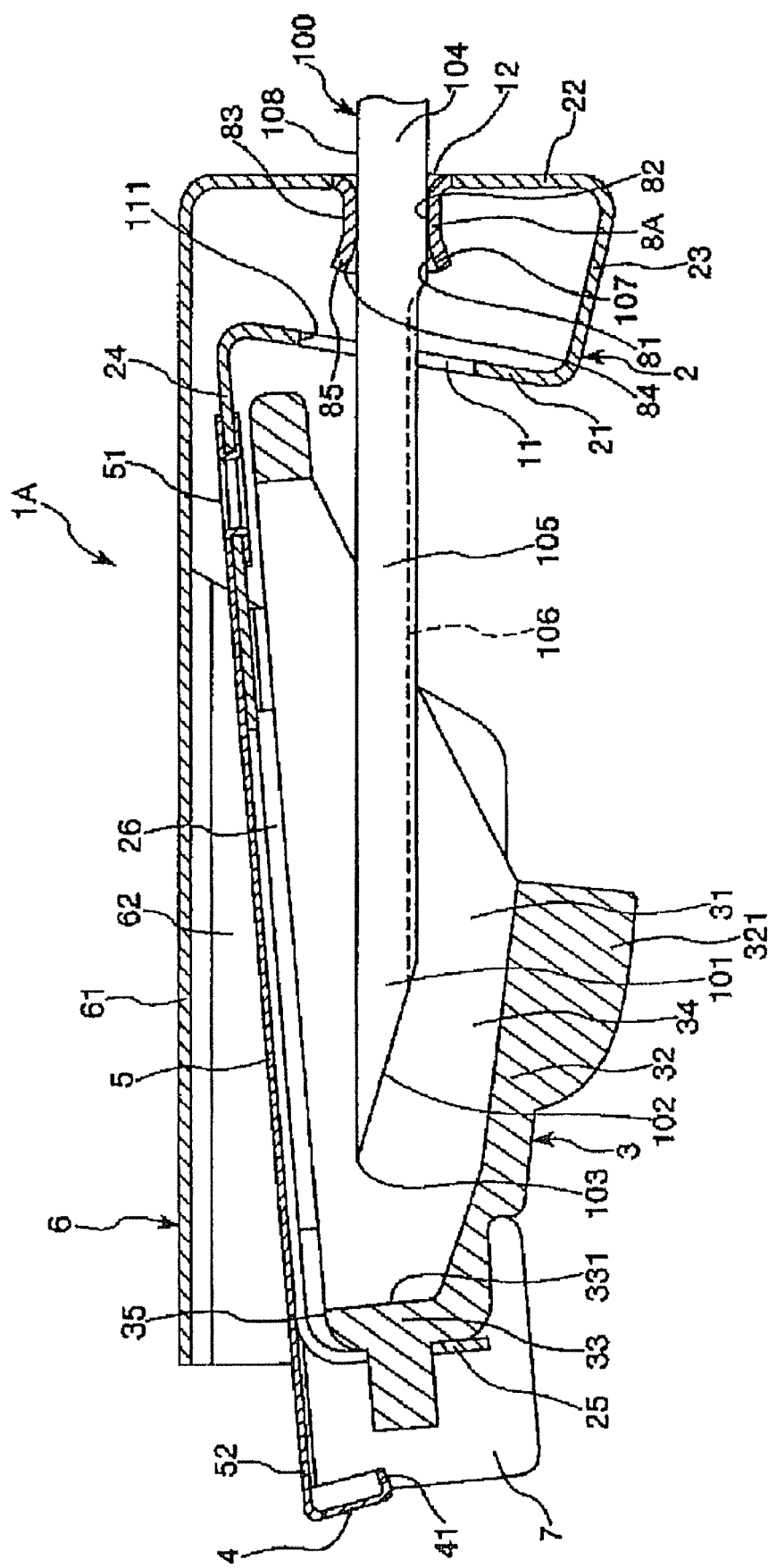
FIG. 6 is a cross-sectional lateral view illustrating a second embodiment (in the second posture) of the protector according to the present invention.

FIG. 6 is a cross-sectional lateral view illustrating a second embodiment (in the second posture) of a protector according to the present invention.

A description will hereinafter be given, with reference to the figure, of the second embodiment of the protector according to the present invention. However, differences between the embodiment described above and the second embodiment shall primarily be described, while explanations of matters, which are the same or common between the embodiments, are omitted.

The present embodiment is the same as the first embodiment, except for the length of the tubular portion.

A tubular portion 8A of a protector 1A shown in FIG. 6 has a length shorter than the interval between the first section 21 and the second section 22. In other words, a leading end 84 is located between the first hole 11 and the second hole 12. The distance between the proximal end 331 of the third wall portion 33 of the cover portion 3 and the leading end 84 of the tubular portion 8A is sufficiently longer than a length from the forwardmost leading end 103 of the needle body 100 to the proximal end 107 of the enlarged-diameter section 105. This causes a certain amount of play to exist, which is adapted to enable shifting of the needle body 100 along the longitudinal direction thereof, when in the second posture. Thus, even in the state shown in FIG. 6, namely, even in the state where the blade surface 102 of the needle tip 101 faces downward, the disadvantage, which was described with reference to the configuration of the first embodiment shown in FIG. 5, can be eliminated. In other words, the needle body 100 is securely shifted until the needle body abutment portion 35 passes the forwardmost leading end 103 of the needle tip 101, thereby providing a state in which the needle tip 101 is reliably covered.

The protector of the present invention has been described thus far with reference to the illustrated embodiments. However, the invention is not limited to the illustrated embodiments. Parts that make up the protector can each be replaced with other parts having configurations that are capable of exhibiting the same or similar functions. Alternatively, various additional structures may be added to the protector.

The protector of the present invention can be attached for use to various types of injection needles, for example, as well as implant needle assemblies.

In the protector constructed as shown in FIG. 5, the distance between the proximal end of the third wall portion of the cover portion and the leading end of the tubular portion is set to a value sufficiently greater than the length from the forwardmost leading end of the needle body to the proximal end of the enlarged-diameter section. This causes an amount of play, which is adapted to allow the needle body to be shifted in a longitudinal direction thereof, when in the second posture. Thus, in the state shown in FIG. 5, namely, even in a state in which the blade surface of the needle tip faces the needle body abutment portion, the aforementioned disadvantage described can be eliminated. In other words, the needle body is shifted securely, until the needle body abutment portion passes the forwardmost leading end of the needle tip, thereby providing a state in which the needle tip is covered reliably.

Industrial Applicability

The protector of the present invention is mounted on a needle body including an elongate main needle body and an enlarged-diameter section provided on a distal side of the main needle body and having an outer diameter greater than that of the main needle body. The protector is shiftable from a first posture capable of relatively moving along a longitudinal direction of the needle body to a second posture covering a needle tip of the needle body. The protector includes a protector body formed by bending or curving an elastic plate-like member made of a metal material and including a first section formed with a first hole adapted to receive the needle body when the needle body is passed therethrough, a second section located on a proximal side of the first section and formed with a second hole adapted to receive the needle body when the needle body is passed therethrough, a third section adapted to connect one end of the first section with the second section, and a fourth section extending from the other end of the first section toward the distal side. The protector also includes a cover portion including a needle tip receiving portion provided on the side of the fourth section of the protector body so as to cover the needle tip from the distal side during the second posture, and a needle body abutment portion that functions to prevent the needle tip receiving portion from covering the needle tip by abutment against an outer circumferential surface of the needle body during the first posture. The second section is provided with a tubular portion formed like a tube to project from a circumferential edge of the second hole toward a distal direction, and to permit the main needle body to pass therethrough while prohibiting the enlarged-diameter section from passing therethrough. The protector is shifted from the first posture in the distal direction relative to the needle body, and the needle body abutment portion passes the needle tip, whereby the protector is deformed by an elastic force of the protector body so as to assume the second posture. In the second posture, the tubular portion comes into abutment against the enlarged-diameter section to thereby prohibit the needle body from shifting toward the distal side. With the protector configured as described above, in the course of shifting from the first posture to the second posture, the tubular portion guides the moving needle body, thereby enabling the needle body to move smoothly. In the second posture, because the tubular portion comes into reliable abutment against the enlarged-diameter section of the needle body, disengagement of the protector from the needle body can be reliably prevented. Thus, the protector of the present invention has industrial applicability.

The invention claimed is:

1. A protector mounted on a needle body including an elongate main needle body and an enlarged-diameter section provided on a distal side of the main needle body and having an outer diameter greater than that of the main needle body, the protector being shiftable from a first posture capable of relatively moving along a longitudinal direction of the needle body to a second posture covering a needle tip of the needle body, the protector comprising:

a protector body formed by bending or curving an elastic plate-like member made of a metal material and including a first section formed with a first hole possessing an inner circumferential surface and having a size that is sufficiently large to receive the needle body without making contact therewith when the needle body is passed therethrough, a second section located on a proximal side of the first section and formed with a second hole adapted to receive the needle body when the needle body is passed therethrough, a third section adapted to connect one end of the first section with the second section, and a fourth section extending from the other end of the first section toward the distal side; and a cover portion including a needle tip receiving portion provided on a side of the fourth section of the protector body so as to cover the needle tip from the distal side during the second posture, and a needle body abutment portion that functions to prevent the needle tip receiving portion from covering the needle tip by abutment against an outer circumferential surface of the needle body during the first posture;

wherein the second section is provided with a tubular portion formed like a tube to project from a circumferential edge of the second hole toward a distal direction, and to permit the main needle body to pass therethrough while prohibiting the enlarged-diameter section from passing therethrough, the tubular portion possessing an outer circumferential surface;

wherein in both the first and second postures, the tubular portion is disposed such that an axis of the tubular portion is parallel to an operating direction in which the needle body is pulled in a proximal direction;

wherein the tubular portion has a minimum inner diameter, which is set to a value greater than an outer diameter of the main needle body and smaller than an outer diameter of the enlarged-diameter section, such that a slight gap is provided between an inner circumferential surface of the tubular portion and an outer circumferential surface of the main needle body;

wherein in both the first and second postures, the outer circumferential surface of the tubular portion is separate from the inner circumferential surface of the first hole, and wherein the protector is shifted from the first posture in the distal direction relative to the needle body and the needle body abutment portion passes the needle tip, whereby the protector is deformed by an elastic force of the protector body so as to assume the second posture, and in the second posture, a distal end portion of the tubular portion comes into abutment against the enlarged-diameter section to thereby prohibit the needle body from shifting toward the proximal side.

2. The protector according to claim 1, wherein the distal end portion of the tubular portion first hole extends distally beyond the first section.

3. The protector according to claim 1, wherein a leading end of the tubular portion is located between the first hole and the second hole.

4. The protector according to claim 1, wherein the tubular portion is made of a metal material.

5. The protector according to claim 1, wherein an inner circumferential surface of the tubular portion is subjected to a friction reducing treatment for reducing frictional resistance between the outer circumferential surface of the needle body and the inner circumferential surface of the tubular portion.

6. The protector according to claim 1, wherein the cover portion is made of a resin material.

7. The protector according to claim 1, further comprising an auxiliary needle tip receiving portion provided on the distal side of the needle tip receiving portion, for receiving the needle tip when the needle tip is about to move across the needle tip receiving portion and project therefrom in the distal direction during the second posture.

8. The protector according to claim 1, wherein the cross-sectional size of the inner circumferential surface of the tubular portion is the same at axially spaced locations of the tubular portion.

9. The protector according to claim 8, wherein a distal end of the tubular portion is outwardly tapered.

10. A protector mounted on a needle body including an elongate main needle body and an enlarged-diameter section provided on a distal side of the main needle body and having an outer diameter greater than that of the main needle body, the protector being shiftable from a first posture capable of relatively moving along a longitudinal direction of the needle body to a second posture covering a needle tip of the needle body, the protector comprising:

a protector body formed by bending or curving an elastic plate-like member made of a metal material and including a first section formed with a first hole possessing an inner circumferential surface and having a size that is sufficiently large to receive the needle body without making contact therewith when the needle body is passed therethrough, a second section located on a proximal side of the first section and formed with a second hole adapted to receive the needle body when the needle body is passed therethrough, a third section adapted to connect one end of the first section with the second section, and a fourth section extending from the other end of the first section toward the distal side; and a cover portion including a needle tip receiving portion provided on a side of the fourth section of the protector body so as to cover the needle tip from the distal side during the second posture, and a needle body abutment portion that functions to prevent the needle tip receiving portion from covering the needle tip by abutment against an outer circumferential surface of the needle body during the first posture;

wherein the second section is provided with a tubular portion formed like a tube to project from a circumferential edge of the second hole toward a distal direction, and to permit the main needle body to pass therethrough while prohibiting the enlarged-diameter section from passing therethrough, the tubular portion possessing an outer circumferential surface;

wherein in both the first and second postures, the tubular portion is disposed such that an axis of the tubular portion is parallel to an operating direction in which the needle body is pulled in a proximal direction;

wherein the tubular portion has a minimum inner diameter, which is set to a value greater than an outer diameter of the main needle body and smaller than an outer diameter of the enlarged-diameter section, such that a slight gap is provided between an inner circumferential surface of the tubular portion and an outer circumferential surface of the main needle body;

wherein the tubular portion passes through and projects from the first hole toward the distal side;

wherein in both the first and second postures, the outer circumferential surface of the tubular portion is separate from the inner circumferential surface of the first hole, and wherein the protector is shifted from the first posture in the distal direction relative to the needle body and the needle body abutment portion passes the needle tip, whereby the protector is deformed by an elastic force of the protector body so as to assume the second posture, and in the second posture, a distal end portion of the tubular portion comes into abutment against the enlarged-diameter section to thereby prohibit the needle body from shifting toward the proximal side.

11. The protector according to claim 10, wherein a leading end of the tubular portion is located between the first hole and the second hole.

12. The protector according to claim 10, wherein the tubular portion is made of a metal material.

13. The protector according to claim 10, wherein an inner circumferential surface of the tubular portion is a surface which has been subjected to a friction reducing treatment so that the inner circumferential surface of the tubular portion exhibits reduced frictional resistance relative to the outer circumferential surface of the needle body.

14. The protector according to claim 10, wherein the cover portion is made of a resin material.

15. The protector according to claim 10, further comprising an auxiliary needle tip receiving portion provided on the distal side of the needle tip receiving portion, for receiving the needle tip when the needle tip is about to move across the needle tip receiving portion and project therefrom in the distal direction during the second posture.

16. The protector according to claim 10, wherein the cross-sectional size of the inner circumferential surface of the tubular portion is the same at axially spaced locations of the tubular portion.

17. The protector according to claim 16, wherein a distal end of the tubular portion is outwardly tapered.

\* \* \* \* \*